United States Patent
Dai et al.

(10) Patent No.: US 10,738,202 B2
(45) Date of Patent: Aug. 11, 2020

(54) POROUS THERMALLY INSULATING COMPOSITIONS CONTAINING HOLLOW SPHERICAL NANOPARTICLES

(71) Applicants: UT-Battelle, LLC, Oak Ridge, TN (US); University of Tennessee Research Foundation, Knoxville, TN (US); Virginia Tech, Blacksburg, VA (US)

(72) Inventors: Sheng Dai, Knoxville, TN (US); Jinshui Zhang, Oak Ridge, TN (US); Xueguang Jiang, Johns Creek, GA (US); Shannon Mark Mahurin, Lenoir, TN (US); Xiao-Guang Sun, Knoxville, TN (US); Huimin Luo, Knoxville, TN (US); Rui Qiao, Blacksburg, VA (US)

(73) Assignees: UT-Battelle, LLC, Oak Ridge, TN (US); University of Tennessee Research Foundation, Knoxville, TN (US); Virginia Tech, Blacksburg, VA (US)

(*) Notice: Subject to any disclaimer, the term of this patent is extended or adjusted under 35 U.S.C. 154(b) by 21 days.

(21) Appl. No.: 15/866,630

(22) Filed: Jan. 10, 2018

(65) Prior Publication Data
US 2018/0194954 A1    Jul. 12, 2018

Related U.S. Application Data

(60) Provisional application No. 62/444,425, filed on Jan. 10, 2017.

(51) Int. Cl.
*C09D 7/62* (2018.01)
*C09D 5/00* (2006.01)
(Continued)

(52) U.S. Cl.
CPC .......... *C09D 7/62* (2018.01); *A61K 9/51* (2013.01); *A61K 31/77* (2013.01); *A61K 33/00* (2013.01);
(Continued)

(58) Field of Classification Search
CPC ........................................................ C09D 7/62
USPC ..................................................... 427/372.2
See application file for complete search history.

(56) References Cited

U.S. PATENT DOCUMENTS 6,800,337 B1 * 10/2004 Siemensmeyer ....... C03C 17/32
                                                    428/1.1
6,986,943 B1 *  1/2006 Cook .......................... B01J 2/30
                                                    427/214
(Continued)

OTHER PUBLICATIONS

Gao, Synthesis and Characterization of Porous Liquids, Masters Thesis, University of Tennessee, Dec. 2016, p. 1-56 (Year: 2016).*
(Continued)

*Primary Examiner* — Tabatha L Penny
(74) *Attorney, Agent, or Firm* — Scully, Scott, Murphy & Presser, P.C.

(57) ABSTRACT

A method of thermally insulating a surface, the method comprising applying a coating of a thermally insulating composition onto said surface, wherein said thermally insulating composition comprises: (i) hollow spherical nanoparticles having a mean particle size of less than 800 nm in diameter and a particle size distribution in which at least 90% of the hollow spherical nanoparticles have a size within ±20% of said mean particle size, and a first layer of cationic or anionic molecules attached to said surfaces of the hollow spherical nanoparticles; and (ii) a second layer of molecules of opposite charge to the first layer of molecules, wherein said second layer of molecules of opposite charge are ionically associated with said first layer of molecules, wherein the molecules in said second layer have at least eight carbon atoms.

24 Claims, 3 Drawing Sheets

(51) Int. Cl.
*C09D 7/40* (2018.01)
*C09D 171/02* (2006.01)
*A61K 33/00* (2006.01)
*A61K 9/51* (2006.01)
*F16L 59/02* (2006.01)
*A61K 31/77* (2006.01)
*C08K 3/36* (2006.01)
*C08K 9/06* (2006.01)
*C08K 7/26* (2006.01)
*C09D 7/61* (2018.01)
*E06B 3/67* (2006.01)

(52) U.S. Cl.
CPC ............... C09D 5/00 (2013.01); C09D 7/70 (2018.01); C09D 171/02 (2013.01); F16L 59/028 (2013.01); C08K 3/36 (2013.01); C08K 7/26 (2013.01); C08K 9/06 (2013.01); C08K 2201/003 (2013.01); C08K 2201/011 (2013.01); C09D 7/61 (2018.01); C09D 7/66 (2018.01); E06B 3/67 (2013.01)

(56) References Cited

U.S. PATENT DOCUMENTS

| | | |
|---|---|---|
| 2004/0077738 A1 | 4/2004 | Field et al. |
| 2007/0199647 A1* | 8/2007 | Benim ............... B65D 23/0878 156/251 |
| 2012/0121886 A1* | 5/2012 | Huang ................. C09D 5/004 428/313.5 |
| 2012/0315423 A1* | 12/2012 | Livacich ............... A62B 17/00 428/41.8 |
| 2014/0059971 A1 | 3/2014 | Jelle et al. |
| 2015/0274538 A1* | 10/2015 | Yuan ................. C08G 73/0206 428/405 |
| 2017/0073237 A1 | 3/2017 | Lim et al. |

OTHER PUBLICATIONS

Gao, Y. "Synthesis and Characterization of Porous Liquids", Master's Thesis, University of Tennessee, (2016), 66 pages. http://trace.tennessee.edu/utk_gradthes/4287.

Zhang, J. et al., "Porous Liquids: A Promising Class of Media for Gas Separation", Angew. Chem. Int. Ed., (2015), 54, pp. 932-936. DOI: 10.1002/anie.201409420.

International Search Report and Written Opinion dated Mar. 8, 2018 issued in PCT/US2018/013071.

Gao, "Synthesis and characterization of porous liquids", Masters Thesis, University of Tennessee. Dec. 2016. Retrieved from the Internet: <URL: http://trace.tennessee.edu/cgi/viewcontent.cgi?article=5531&context=utk_gradthes>.

* cited by examiner

POROUS THERMALLY INSULATING COMPOSITIONS CONTAINING HOLLOW SPHERICAL NANOPARTICLES

CROSS REFERENCE TO RELATED APPLICATION

The present application claims benefit of U.S. Provisional Application No. 62/444,425, filed on Jan. 10, 2017, all of the contents of which are incorporated herein by reference.

STATEMENT REGARDING FEDERALLY SPONSORED RESEARCH

This invention was made with government support under Prime Contract No. DE-AC05-00OR22725 awarded by the U.S. Department of Energy. The government has certain rights in the invention.

FIELD OF THE INVENTION

The present invention relates generally to thermally insulating or soundproofing compositions, and more particularly, to such compositions that are porous and that can be applied as a coating on a surface.

BACKGROUND OF THE INVENTION

Traditional solid aerogels used in window-insulation materials generally need to be packed within a specially designed housing, such as in a polymer double skin-sheet between two gaps and two glass panes, or casted in thicker inhomogeneous polymer films. The need for such specialized housings places significant constraints on such materials. Moreover, conventional thermal insulating materials are known to suffer from low transparency, often as a result of the presence of pore sizes or particles above 800 nm or the presence of pores or particles having a broad distribution of sizes (e.g., 400 to 1200 nm). In some instances, the thermal insulating materials possess acceptable transparency when first installed, but experience a gradual deterioration of the transparency over time (and hence, a gradual increase in opacity over time) due to aggregation of pores or particles in the material over time. Thus, there would be a significant benefit in a thermal insulating material that does not require a special housing, that can be applied onto a variety of surfaces by simple means to thermally insulate such surfaces, and that exhibits an improved stability by resisting aggregation and thereby retaining an acceptable level of transparency through the lifetime use of the material.

SUMMARY OF THE INVENTION

The present disclosure is particularly directed to a novel method of fabricating thin insulating coatings or films of porous liquids possessing substantial homogeneity and exceptional transparency. The method includes applying a coating of the thermally insulating composition onto a surface of a material for which thermal insulation is desired. The thermally insulating composition includes the following components: (i) hollow spherical nanoparticles having a mean particle size of less than 800 nm in diameter and a particle size distribution in which at least 90% of the hollow spherical nanoparticles have a size within ±20% of the mean particle size, and a first layer of cationic or anionic molecules attached to the surfaces of the hollow spherical nanoparticles; and (ii) a second layer of molecules of opposite charge to the first layer of molecules, wherein the second layer of molecules of opposite charge are ionically associated with the first layer of molecules, wherein the molecules in the second layer have at least eight carbon atoms. In more particular embodiments, the thermally insulating composition includes the following components: (i) hollow spherical nanoparticles having a mean particle size of less than 800 nm in diameter and a particle size distribution in which at least 90% of the hollow spherical nanoparticles have a size within ±20% of the mean particle size, with surfaces of the hollow spherical nanoparticles containing pores having a size of up to or less than 50 nm, and a layer of cationic molecules attached to the surfaces of the hollow spherical nanoparticles; and (ii) a layer of anionic molecules ionically associated with the layer of cationic molecules, wherein the anionic molecules have at least eight carbon atoms.

In particular embodiments, the porous insulating liquid contains a layer of positively-charged organosilane molecules (i.e., "corona") bound to surfaces of hollow silica (HS) nanospheres, and a layer of negatively-charged poly (ethylene glycol) (PEG)-tailed sulfonate molecules (i.e., "canopy") ionically associated with the corona layer. The resulting insulating liquid is optically transparent, nonvolatile, thermally stable, and homogeneous. As the porosity of these porous liquids can exceed those of traditional aerogels, some of the drawbacks associated with existing solid aerogel technologies can be mitigated. The HS nanospheres and polymeric canopy species form ion pairs and behave as ionic compounds, which leads to a highly homogenous material and resists aggregation of hollow particles during film processing. HS nanospheres, particularly those with cavity sizes less than 500, 200, or 100 nm and with a narrow particle size distribution, provide a significantly reduced thermal conductivity of the resulting coating or film without interfering with visible light. Following the same synthesis strategy, transparent, homogeneous, and thermally stable porous liquid coatings, films, and adhesives can be fabricated by tuning the respective corona and canopy species.

The method described herein is useful, by a first embodiment, in producing thermally insulating liquids that flow at room temperature by virtue of the PEG canopy, which generally has a low $T_g$ and melting point ($T_m$) and provides weakened ionic interactions. By another embodiment, higher viscosity porous liquid adhesives and films can be produced by using higher $T_g$ polymers as a canopy material. The porous liquid materials described herein have several advantages as transparent thermal barriers, including: 1) hollow nanoparticles of small size (e.g., less than 800, 500 or 100 nm) and narrow size distribution decrease the thermal conductivity of the material significantly (i.e., due to the "Knudsen effect," the use of smaller nanoparticles further lowers the thermal conductivity); 2) the porous liquid adhesives and films are highly optically transparent since the pores on the particles are much smaller than the average wavelength of visible light; 3) the porous liquids may behave as ionic liquids with substantial homogeneity; 4) the porous liquid adhesives and films provide a comprehensive solution for applied thermal barrier products, and the films are also compatible with low emissive coatings; 5) the concept may also be used to make organic glass; and 6) the porous compositions may also possess significant soundproofing properties.

DETAILED DESCRIPTION OF THE INVENTION

The present disclosure is foremost directed to a method of thermally insulating a surface. In the method, a coating of a thermally insulating composition, as further described below, is applied onto the surface. The surface can belong to any object or material for which thermal insulation or soundproofing is desired. In a first embodiment, the material being coated with the thermally insulating composition is glass, wherein the glass may be part of a window or a pane or sheet of glass to be installed into or manufactured as a window or other functional object. In a second embodiment, the material being coated is a structural material, wherein the structural material is any material that may ordinarily be used to provide structure (e.g., wall, ceiling, tiles, or flooring material) to the interior space where people dwell, reside, or work. In a third embodiment, the material being coated is a paper or plastic product useful in holding a food or beverage (e.g., a cup, drinking glass, or food container). The paper or plastic product may be in the shape of the food or beverage article when coated, or the paper or plastic product may be in a raw or precursor (bulk) form when coated, and then subsequently shaped into the paper or plastic product. In a fourth embodiment, the material being coated is a fabric, particularly a fabric used in clothing. The fabric may be clothing or a textile article for which thermal insulation could be useful (e.g., a pot holder), or the fabric may be in precursor (bulk) form when coated, and then subsequently used to make the clothing or textile. In a fifth embodiment, the material being coated is a metal, such as for a metal pipe. In a sixth embodiment, the material being coated is skin of a mammal (typically a person), in order to provide thermal insulation to the mammal.

The thermally insulating composition can be coated onto a surface by any of the means well known in the art for applying a coating of a liquid onto a surface. The liquid composition may be, for example, brush coated (i.e., painted), spray coated, dip coated, or spin coated onto a surface. The foregoing methods are primarily suitable for coating with a liquid. For more viscous versions of the thermal insulating composition, the composition may still be applied by, for example, brush, dip, or spin coating. However, for tacky, gel-like, or rubbery versions of the thermal insulating composition, the composition may be applied by, for example, forming a film of the composition (e.g., by pouring a liquid form onto a surface or into a mold, leveling, and allowing to harden) and adhering the resulting film onto a surface. The film may be adhered by, for example, application of pressure and/or heat on the film while on the surface being coated, or by using an intermediate adhesive.

The hollow spherical nanoparticles are hollow by containing an encapsulated space not occupied by a solid or liquid. Generally, the hollow nanoparticles encapsulate a gas, such as air or other gas (e.g., nitrogen or argon). Nevertheless, the present disclosure contemplates embodiments in which the hollow nanoparticles encapsulate a space under reduced pressure (i.e., less than 1 atm) or under partial vacuum (e.g., 0.1 atm or less). The term "spherical," as used herein, is meant to encompass any shape that is either perfectly spherical or approaching a spherical shape, which includes elliptical (i.e., oval) shapes, except that the elliptical shape should have a degree of eccentricity of no more than 0.5, 0.4, 0.3, 0.2, or 0.1. The hollow spherical nanoparticles have a mean (average) particle size of less than 800 nm in diameter. The particle size generally refers to the diameter of the nanoparticle, wherein the diameter generally refers to the length through the midpoint of the nanoparticle from surface end to surface end. As the foregoing definition of the particle size includes the wall thickness, the diameter of the inner hollow portion (inner diameter) is necessarily smaller than the nanoparticle size or diameter as defined above. If not a perfect sphere, the term "diameter" generally refers to an average diameter of the short and long dimensions of the nanoparticle. In different embodiments, the nanoparticles have a particle size of up to (no more than) or less than 750, 700, 600, 500, 400, 300, 250, 200, 150, or 100 nm, or a particle size within a range bounded by any two of the foregoing values. The wall thickness is typically no more than 20, 10, 5, 2, or 1 nm or within a range between any of the foregoing values.

For purposes of the invention, the hollow spherical nanoparticles should have a substantial degree of uniformity in size. The substantial degree of uniformity is particularly advantageous for rendering the thermally insulating composition substantially or completely transparent. The degree of uniformity can be expressed as a constraint on the distribution of particle sizes relative to the average particle size. For purposes of the invention, at least 90%, 95%, 98%, 99%, or 100% (all) of the nanoparticles have particle sizes that are within ±20% of the mean particle size. Conversely, up to or less than 10%, 5%, 2%, 1%, or 0% of the nanoparticles have particle sizes that are beyond ±20% of the mean particle size. As an example, a population of hollow spherical nanoparticles having an average particle size of 200 nm should have a particle size distribution in which at least 90% of the particles have a size within a size range of 160-240 nm, which is within ±20% of the average particle size of 200 nm. Conversely, 10% or less (e.g., 5%, 2%, 1%, or 0%) of the nanoparticles are permitted to have a size less than 160 nm and/or greater than 240 nm in the foregoing example.

The hollow spherical nanoparticles can have any solid composition that is sufficiently resilient that it can maintain a spherical shape even when a slight, moderate, or significant amount of pressure is applied. In particular embodiments, the hollow nanoparticles can be constructed of any solid material with sufficient mechanical strength to resist rupture, flattening, or significant deformation when subjected to a substantial force or pressure, e.g., at least 0.001, 0.01, 0.1, 1, 2, or 5 GPa. The composition of the nanoparticles can be inorganic (e.g., an oxide, sulfide, or nitride) or organic (e.g., a polymer). The composition of the nanoparticles is preferably substantially or completely transparent in order to render the thermally insulating composition substantially or completely transparent.

In one set of embodiments, the hollow spherical nanoparticles have a metal oxide composition. The metal in the metal oxide can be or include any suitable metal, such as, for example, a main group, transition metal, or lanthanide metal. The hollow metal oxide structure is preferably transparent. Some examples of main group metal oxide compositions include oxides of Groups 13-15, such as $SiO_2$ (i.e., "silicon oxide" or "silica"), $Al_2O_3$ (i.e., "aluminum oxide" or "alumina"), $B_2O_3$, $Ga_2O_3$, $SnO_2$, $Sb_2O_3$, $Sb_2O_5$, and $Bi_2O_3$. Some examples of transition metal oxide compositions include oxides of Groups 3-12, such as $Sc_2O_3$, $TiO_2$, $ZnO$, $Y_2O_3$, $ZrO_2$, $Nb_2O_5$, $HfO_2$, and $Ta_2O_5$. Some examples of lanthanide oxide compositions include oxides of elements having an atomic number of 55 to 71, e.g., $La_2O_3$, $CeO_2$, $Nd_2O_3$, $Eu_2O_3$, and $Gd_2O_3$. The metal oxide may also be a complex metal oxide by including more than one metal, such as a spinel metal oxide (e.g., $CoMn_2O_4$, $ZnMn_2O_4$, $Zn_xCo_{3-x}O_4$, or $LiNi_{0.5}Mn_{1.5}O_4$) or perovskite metal oxide (e.g., $CaTiO_3$, $BaTiO_3$, and $La_{0.8}Sr_{0.2}MnO_3$).

Numerous and diverse methods for preparing these metal oxide hollow nanostructures are well known in the art. The synthesis of hollow silica nanoparticles is described, for example, in Zhang et al., *Angew. Chem. Int. Ed.*, 54, 932-936 (2015); Yan et al., *Scientific Reports*, 3, 1568 (2013); Nandiyanto et al., *Langmuir*, 28(23), pp. 8616-8624 (2012); Fuji et al., *Advanced Powder Technology*, 23(5), pp. 562-565 (September 2012); Chen et al., *Biomaterials*, 25(4), 723-7, 2004; and Hah et al., *Chem. Commun.*, pp. 1712-1713 (2003), the contents of which are herein incorporated by reference in their entirety. The synthesis of hollow aluminum oxide or aluminum oxide hydroxide nanoparticles is described, for example, in Lozhkomoev et al., *Nanotechnology*, 27(20), (2016); Smovzh et al., *Advances in Nanoparticles*, 2, pp. 120-124 (2013); Lee et al., *Thin Solid Films*, vol. 529, pp. 394-397, February 2013; and Wang et al., *Journal of the American Ceramic Society*, vol. 92: S32-S37 (2009), the contents of which are herein incorporated by reference in their entirety. The synthesis of hollow nanostructures constructed of $SnO_2$, $TiO_2$, $Fe_2O_3$, and $Co_3O_4$ is described, for example, in Wang et al., *Advanced Materials*, 24(14), pp. 1903-1911, April 2012 and Wu et al., *Nanoscale*, 4, pp. 2526-2542 (2012), the contents of which are herein incorporated by reference in their entirety. The synthesis of hollow nanostructures constructed of $Nb_2O_5$, $CeO_2$, and $V_2O_5$ is described, for example, in Liu et al., *Inorg. Chem.* 48(9), 3898-3900 (2009), the contents of which are herein incorporated by reference in their entirety. The synthesis of hollow nanostructures constructed of mixed metal oxides is described, for example, in Wang et al., *Advanced Materials*, 24(14), pp. 1903-1911, April 2012; Wu et al., *ACS Nano*, 8(6), pp. 6297-6303 (2014); and Lu et al., *Journal of Power Sources*, 271, pp. 55-59 (2014), the contents of which are herein incorporated by reference in their entirety.

The hollow spherical nanoparticles may alternatively have a metal sulfide composition, which may be a sulfur-substituted version of any of the metal oxide compositions provided above (for example, ZnS). The synthesis of hollow nanoparticles having a metal sulfide composition is described, for example, in Niu et al., *Langmuir*, 26(22), pp. 16652-16657 (2010); Guo et al., *ACS Nano*, 7(10), pp. 8780-8793, 2013; and Xu et al., *Ultrasonics Sonochemistry*, 13(5), pp. 451-454, July 2006; the contents of which are herein incorporated by reference in their entirety.

The hollow spherical nanoparticles may alternatively have a metal nitride composition, particularly a main group (e.g., Group 13) metal nitride composition. The synthesis of hollow boron nitride nanospheres is described, for example, in Li et al., *Nat. Commun.*, 8:13936 (2017); Bernard et al., *J. Mater. Chem.*, 21 (24), 8694-8699 (2011); and Zhang et al., *Journal of Nanomaterials*, 2009, Article ID 264026, 4 pages, doi: 10.1155/2009/264026 (2009), the contents of which are herein incorporated by reference in their entirety. The synthesis of hollow aluminum nitride nanospheres is described, for example, in Zheng et al., *Journal of Solid State Chemistry*, 280 (1), 276-283 (2007) and Ma et al., *J. Mater. Chem.*, 16, 2834-2838 (2006), the contents of which are herein incorporated by reference in their entirety. The synthesis of hollow gallium nitride nanospheres is described, for example, in Pan et al., *Chem. Mater.*, 18 (23), 5392-5394 (2006), the contents of which are herein incorporated by reference in their entirety. The synthesis of hollow silicon nitride nanospheres is described, for example, in Lu et al., *Applied Ceramic Technology.*, 12 (5), 939-948 (2015), the contents of which are herein incorporated by reference in their entirety.

In other embodiments, the hollow spherical nanoparticles include or are completely constructed of a polymer composition, which may be crosslinked or uncrosslinked. The polymer may be organic, inorganic, or a combination thereof (i.e., hybrid). The organic polymer hollow nanostructure can be, for example, based on maleic anhydride and divinylbenzene (DVB), such as described in Deng et al., *J. Phys. Chem. B*, 114(8), pp. 2593-2601 (2010), the contents of which are herein incorporated by reference in their entirety. The organic polymer hollow nanostructure may alternatively be based on divinylbenzene reaction with either methyl methacrylate (MMA) or styrene, such as described in Itou et al., *Colloids and Surfaces A: Physicochemical and Engineering Aspects*, 153(1-3), pp. 311-316 (1999) and Li et al., *Scientific Reports*, 3, no. 2128 (2013), the contents of which are herein incorporated by reference in their entirety. The organic polymer hollow nanostructure may alternatively be constructed of poly(lactic-co-glycolic)acid (PGLA), such as described in Raichur et al., 1(4), *Mater. Res. Express*, 045407. doi:10.1088/2053-1591/1/4/045407 (2014), the contents of which are herein incorporated by reference in their entirety. The organic polymer hollow nanostructure may alternatively be prepared by reaction of poly(4-vinylpyridine) (P4VP) with poly(amic acid) ester, such as described in Chen et al., *Acc. Chem. Res.*, 38(6), pp. 494-502 (2005), the contents of which are herein incorporated by reference in their entirety. In the case of an inorganic or hybrid organic-inorganic (hybrid) polymer nanostructure, the polymer may, in one embodiment, be in the form of crosslinked polyphosphazene nanospheres, such as described in Liu et al., *Journal of Materials Chemistry*, 21(34), p. 12964-12968 (2011), the contents of which are herein incorporated by reference in their entirety. Hollow polyphosphazene microspheres are also described in, for example, Wang et al., *RSC Advances*, 5, 33720-33728 (2015), the contents of which are herein are incorporated by reference in their entirety. In another embodiment, the hybrid polymer composition may be in the form of hollow polysiloxane nanospheres, such as described in Wang et al., *Journal of Materials Chemistry*, 14, pp. 1648-1651 (2004), the contents of which are herein incorporated by reference in their entirety. In some embodiments, the polymeric hollow nanostructures are semiconductive, such as described in, for example, Landester et al., *Advanced Materials*, 14(9), pp. 651-655 (2002), the contents of which are herein are incorporated by reference in their entirety.

The hollow spherical nanoparticles may be porous or non-porous. Typically, as a result of the synthetic procedure, the hollow nanoparticles possess some level of porosity. For purposes of the invention, in the event the hollow nanoparticles are porous, the pores should have a size of no more than (i.e., up to or less than) 50 nm to ensure that molecules (e.g., solvent molecules or species being bound to the nanoparticles surface) do not enter the hollow cavities of the nanoparticles. The pores preferably have a size less than 50 nm, and even more preferably, a size up to or less than 40, 30, 20, 10, or 5 nm. In preferred embodiments, the pores are exclusively micropores, i.e., pore size up to or less than 2 nm or 1 nm.

A layer of cationic molecules (herein referred to as the "first layer") is attached to surfaces of the hollow spherical nanoparticles. The cationic molecules are attached to the surfaces of the hollow nanoparticles by any bonding mode (e.g., covalent, ionic, hydrogen, or van der Waals bonding) that maintains attachment and prevents detachment of the cationic molecules from the surface. The cationic molecule can be any molecule having at least one positively charged functional group and which is bound to the surface of the nanoparticle. The cationic molecule can be, for example, a silane molecule containing one or more positively charged groups. Silane molecules possessing alkoxy groups (typically methoxy and ethoxy groups) attached to the silicon atom by an Si—O bond are particularly suited for bonding onto surfaces bearing hydroxy groups (i.e., M-OH, where M is a metal of the hollow nanoparticle) via condensation of the alkoxy group (i.e., elimination of methanol or ethanol) and simultaneous formation of a M-O—Si bond. As many of the metal oxide compositions (e.g., silica and alumina) contain surface hydroxy groups, silane molecules containing alkoxy groups are suitable for bonding to a range of metal oxide nanoparticles.

In particular embodiments, the cationic molecule is a silane molecule having the following structural motif: $(RO)_3Si$—$(CH_2)_n$—$N^+R^1R^2R^3$, wherein R can be any hydrocarbon group, but more typically, methyl or ethyl, except that, once bonded, at least one of the R groups should be a covalent bond to a surface metal atom. The groups $R^1$, $R^2$, and $R^3$ can be a hydrogen atom or a hydrocarbon group. Typically, at least one or two of $R^1$, $R^2$, and $R^3$ are long chain alkyl groups containing at least 6, 8, 10, 12, 14, or 16 carbon atoms. The subscript n is typically at least 2, 3, or 4. Numerous such cationic silanes are described in, for example, EP0108853 and U.S. Pat. No. 3,730,701, the contents of which are herein incorporated in their entirety by reference. Some examples of such silane molecules containing positively charged groups include N,N-didecyl-N-methyl-N-(3-trimethoxysilylpropyl)ammonium, N-octadecyl-N,N-dimethyl-N-(3-trimethoxysilylpropyl)ammonium, N-tetradecyl-N,N-dimethyl-N-(3-trimethoxysilylpropyl) ammonium, 4-(trimethoxysilylethyl)benzyltrimethylammonium, and N-trimethoxysilylpropyl-N,N,N-trimethylammonium. The cationic molecule may alternatively be, for example, a molecule containing one or more phosphonium groups. An example of a molecule containing the phosphonium group includes, for example, a silane containing a phosphonium group, such as 2-(triphenylphosphonium)ethyldimethyl-triethoxysilane. The cationic molecule may alternatively be a molecule containing one or more iminium or sulfonium groups.

In other embodiments, the cationic molecules are cationic polymers. The cationic polymer may contain one or more ammonium, iminium, phosphonium, or sulfonium groups. Such polymers typically bond to the nanoparticle surface by ionic, van der Waals, and/or hydrogen bonding. However, the polymer may bond covalently in some cases, such as in the case of polysiloxanes, which may have a structure similar to those exemplified above except for the presence of Si—O—Si bonds, with some or all of the Si atoms attached to a positively charged group. Some examples of other cationic polymers include polylysine, chitosan, protonated polyaniline, and quaternized polyethylenemine. The polymer containing ammonium, iminium, phosphonium, or sulfonium groups may alternatively be a dendrimer containing such groups. The polymer containing ammonium, iminium, phosphonium, or sulfonium groups may alternatively be an ionomer containing such groups. The cationic molecule or polymer preferably has a length, from bonding site on the nanoparticle to terminal end, of at least 1 nm, 1.5 nm, 2 nm, 2.5 nm, or 3 nm.

A layer of anionic molecules (herein referred to as the "second layer") is ionically associated (i.e., ionically paired) with the layer of cationic molecules. It is understood that the second layer resides on top of the first layer, and thus, the second layer is located a further distance from the surface of the hollow nanoparticle than the first layer. The term "ionically associated" indicates that the total positive charge of the layer of cationic molecules is counterbalanced by the total negative charge of the layer of anionic molecules, analogous to the counterbalancing of positively and negatively charged species in a salt. For purposes of the invention, the anionic molecule can be any molecule having at least one negatively charged functional group and that possesses at least or more than six, eight, ten, or twelve carbon atoms. Typically, at least a portion of the carbon atoms are engaged in C—H bonds. The anionic molecules may be polymeric or non-polymeric. The negatively charged functional group can be any such groups known in the art, such as a sulfonate, sulfate, carboxylate, phosphonate, phosphate, or alkoxylate group. In some embodiments, the anionic molecule includes a polyalkylene oxide (e.g., polyethylene oxide, or polyoxyethylene) segment, which may contain at least 1, 2, 3, 4, 5, 8, 10, 12, 15, or 20 alkylene oxide units. The anionic molecule may or may not include a carbocyclic saturated or unsaturated group (e.g., cyclohexyl or phenyl ring), and may or may not include a long chain alkyl group containing at least six, seven, eight, nine, ten, eleven, or twelve carbon atoms. In some embodiments, the anionic molecule is any one of the well known long-chain anionic surfactants, such as those based on lauryl ether sulfate. In some embodiments, the anionic molecule contains a long alkyl segment and a negatively charged group. Some examples of such molecules include dodecylsulfate, octylsulfate, nonylsulfonate, oleate, and palmitate, and alternative versions of these molecules containing a carbocyclic ring and/or polyoxyethylene segment. In the case of an anionic polymer, the anionic polymer may, in some cases, be an anionic dendrimer or ionomer. The anionic molecule preferably has a length of at least or greater than 1 nm, 1.5 nm, 2 nm, 2.5 nm, or 3 nm.

In some embodiments, the porous insulating composition behaves as a room temperature ionic liquid by itself, i.e., in the absence of a dissolving solvent. The ionic liquid is typically a liquid at room temperature (e.g., 15, 18, 20, 22, 25, or 30° C.) or lower. In some embodiments, the ionic liquid is a liquid at or below 10, 5, 0, −10, −20, −30, or −40° C.

The porous insulating composition described above can be synthesized by any suitable means. First, the hollow spherical nanoparticles (hollow nanostructures) need to be procured, either commercially or by producing them by any of the means well known in the art. Then, cationic molecules are attached to the hollow nanostructures by means available in the art, such as by reaction of metal oxide hollow nanostructures with a cationic silane molecule containing silicon-bound alkoxy groups and a positively charged group. Alternatively, cationic molecules, such as cationic polymers, may be adsorbed onto the surfaces of the hollow nanostructures. In the event covalent attachment of a cationic species onto a non-oxide hollow nanostructure is desired, other binding chemistries are available, which may involve an initial surface functionalization with groups capable of forming a covalent bond with the cationic molecule. For example, in the case of boron nitride hollow nanostructures, the boron nitride surface may be plasma treated to functionalize the surface, such as with amine groups, as described in, for example, Dai et al., *Nanotechnology*, 22(24), 2011 or Ikuno et al., *Solid State Communications*, 142, 643-646, 2007, or the boron nitride surface may be reacted with ammonia or organoamines to functionalize the surface with any of a variety of functional groups, as described in, for example, Wu et al., *J. Am. Chem. Soc.*, 128(36), 12001-12006, 2006). In the event of amine groups being present on the nanoparticle surface, a cationic molecule having an amine-reactive group (e.g., an aldehyde or ester group) can be reacted with the amine groups to bond the cationic molecules covalently to the nanoparticle surface. Following the attachment of the cationic molecules, anionic molecules are attached to the layer of cationic molecules by means well known in the art, such as by simple contact to establish ionic pairing with the cationic molecules, and removal of excess anionic molecules.

Notably, although the foregoing description of the thermally insulating composition has been related as a first layer of cationic molecules directly attached to the hollow nanoparticles, and a second layer of anionic molecules ionically associated with the cationic molecules, the present disclosure also includes the possibility of a layer of anionic molecules (alternative "first layer") directly attached to the hollow nanoparticles, and a layer of cationic molecules (alternative "second layer") ionically associated with and covering the anionic layer. That is, the present disclosure envisions the possibility of the first and second layers interchanging. In particular embodiments, when the first layer is anionic, the anionic molecule is an anionic silane, such as an alkoxy silane containing a carboxylate or sulfonate group, a number of which are commercially available. Analogous to the cationic silanes described above, the anionic silane can attach to a metal oxide surface to provide the initial layer of anionic molecules. Alternatively, the anionic molecule attaching to the nanoparticle surface is an anionic polymer, as described above. Likewise, if the cationic molecules are used as the second layer, there is no need for them to include reactive groups (such as alkoxy-silyl moieties) useful for covalent attachment to the hollow nanoparticle surface. In some embodiments, particularly when used as a second layer, the cationic molecules may be ammonium-containing molecules containing a long alkyl and/or alkylene oxide segment, in analogy to the anionic molecules described above except that the anionic groups are replaced with cationic groups. Of further note, although the porous composition described above has been mainly described as a flowing or brushable liquid, the porous composition may be prepared as a highly viscous liquid, such as a gel or adhesive, by an appropriate increase in size of the first and/or second layer molecules and/or by selecting the first and/or second layer molecules as more rigid (less flexible) molecules, such as by including more ring moieties in these molecules.

Examples have been set forth below for the purpose of illustration and to describe certain specific embodiments of the invention. However, the scope of this invention is not to be in any way limited by the examples set forth herein.

EXAMPLES

Preparation and Analysis of a Thermally Insulating Composition

Figure 1A:
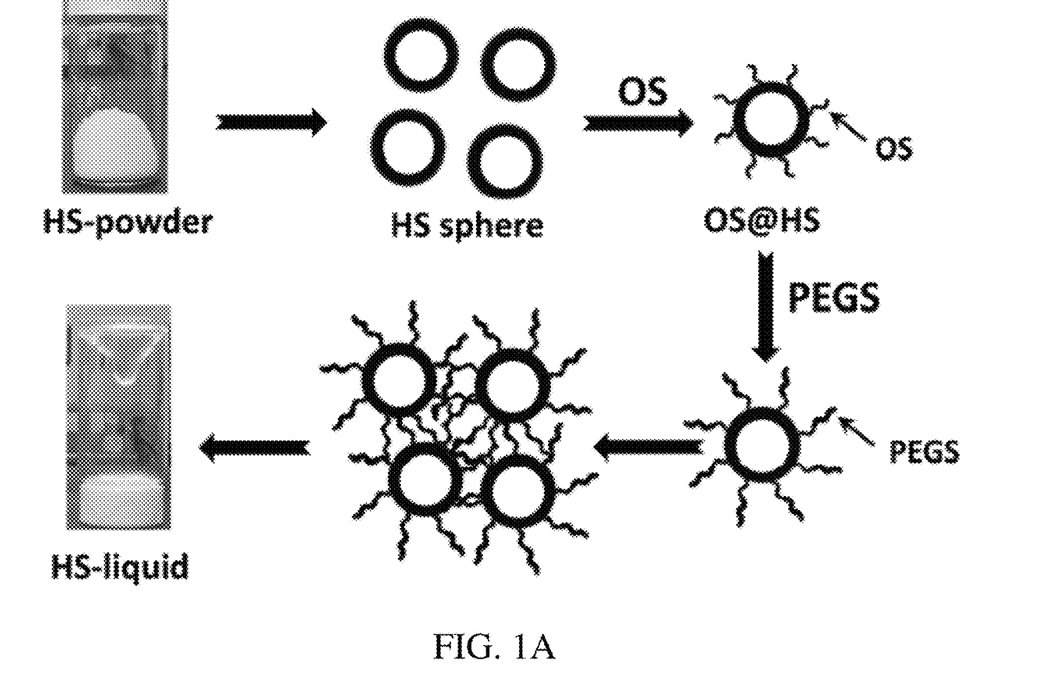
FIG. 1A is a general schematic of a two-step synthetic process used herein to produce a porous liquid containing porous hollow silica spheres.

A Type I porous liquid based on hollow silica (HS) spheres was fabricated in a two-step synthetic procedure according to the general scheme shown in FIG. 1A. In order to preserve the hollow structures in the liquid state, it was found necessary to prevent the fluid medium from filling the cavities. HS spheres with microporous shells that block species larger than 1.9 nm were first synthesized as the core particles. Then the particle surface was modified with a positively charged organosilane (OS) moiety with molecular size larger than 2.0 nm as the corona. In particular experiments, the positively charged OS molecule was $(CH_3O)_3Si(CH_2)_3N^+(CH_3)(C_{10}H_{21})_2Cl^-$. In these steps, the OS molecules selectively react with hydroxyl groups bound to the silica shell surface, which leads to a permanent covalent attachment of a corona layer onto the hollow particles (denoted by OS@HS). The chloride counter anion balancing the positive corona was then replaced by a negatively charged poly(ethylene glycol)-tailed sulfonate (PEGS) canopy, yielding an optically transparent porous liquid (denoted as HS-liquid) at room temperature that can be considered as a novel room temperature ionic liquid (RTIL) with intrinsic and permanent porosity.

Figure 1B:
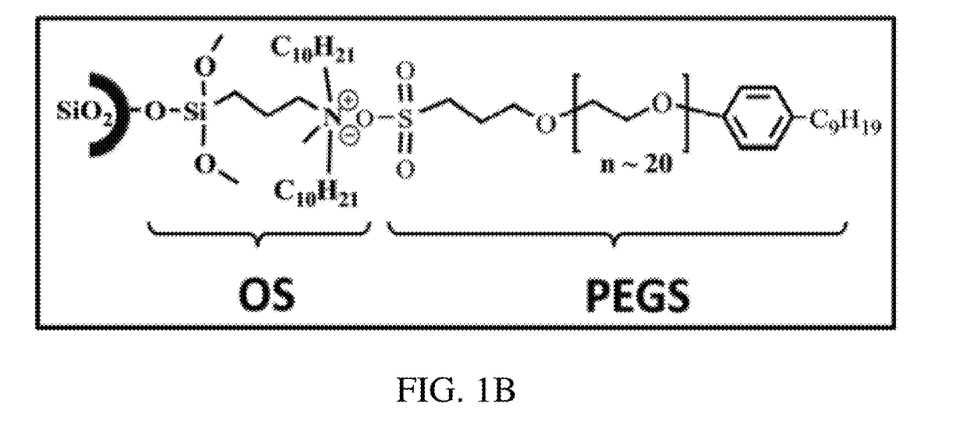
FIG. 1B is a structural representation of first and second layer molecules surrounding the hollow silica spheres. The exemplified process can be extended to hollow nanospheres and first and second layers having numerous other compositions.
Figure 2:
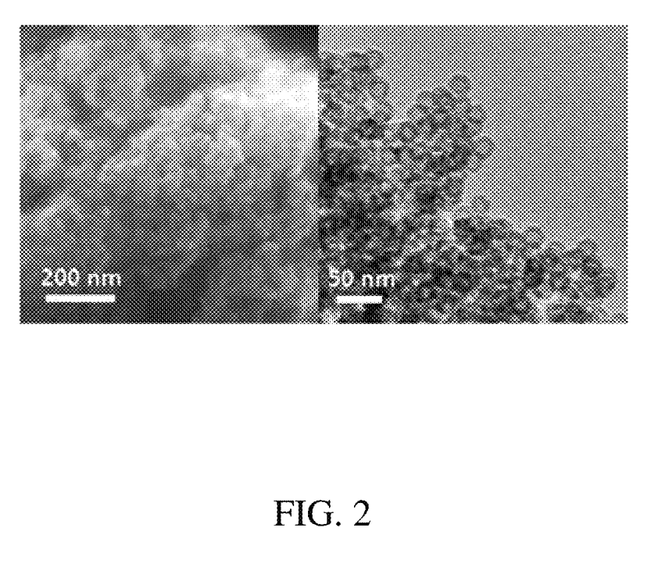
FIG. 2 provides a scanning electron microscopy (SEM) image (left pane) and transmission electron microscopy (TEM) (right pane) of the porous liquid shown in FIG. 1B.
Figure 3:
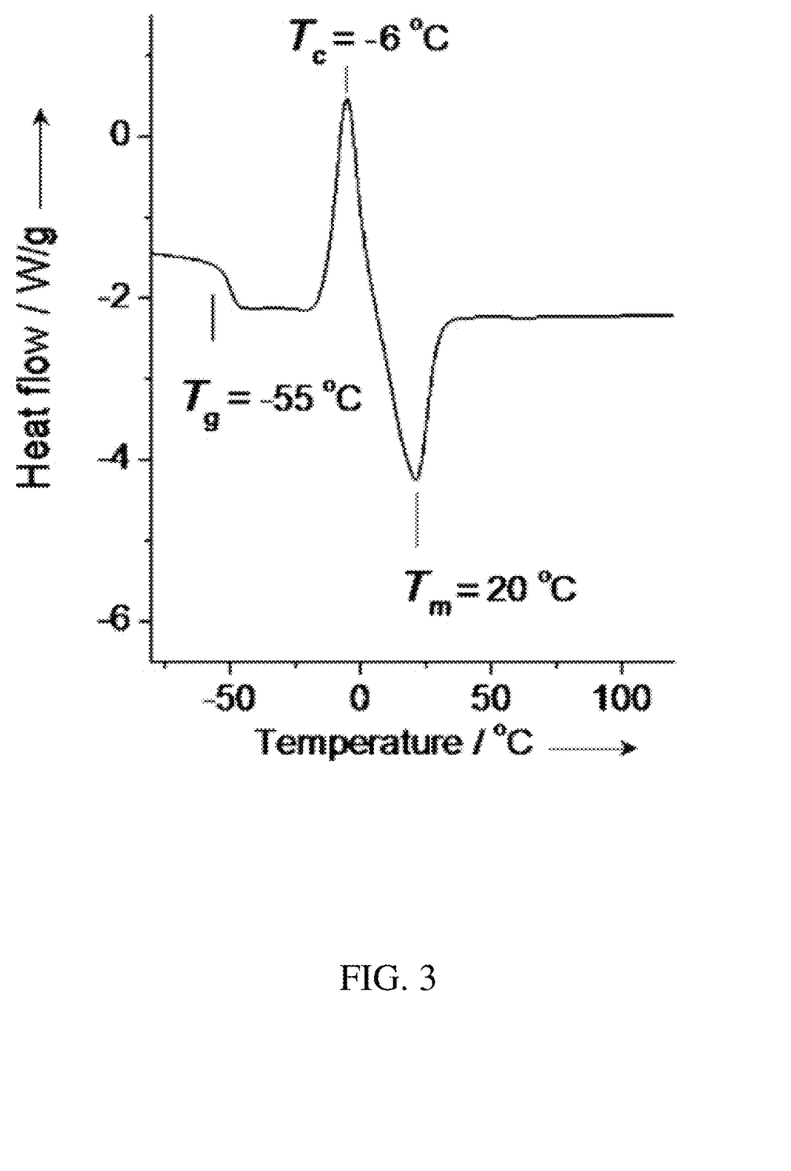
FIG. 3 provides a differential scanning calorimetry (DSC) curve for the porous liquid shown in FIG. 1B along with identification of the $T_g$ values in the curve.

The structure of the resulting porous liquid and the specific poly(ethylene glycol)-tailed sulfonate species used are shown in FIG. 1B. The nanostructure of the porous liquid was imaged by scanning electron microscopy (SEM) and transmission electron microscopy (TEM), and the images are provided in FIG. 2, in left and right panes, respectively. In such an organic-inorganic hybrid fluid, the hollow particles are homogeneously combined with an organic suspending medium (ionic corona-canopy species) into one homogeneous system, which is quite distinguished from that of conventional colloidal suspensions, where the particles and solvents are physically distinct entities. Benefiting from the chemical structure and low $T_g$ of the PEG-based polymeric canopy, the HS-liquid behaves as a flow liquid with negligible vapor pressure at room temperature and relatively high thermal stability (up to −260° C.). A differential scanning calorimetry (DSC) curve for the porous liquid is provided in FIG. 3 along with identification of the $T_g$ values in the curve.

While there have been shown and described what are at present considered the preferred embodiments of the invention, those skilled in the art may make various changes and modifications which remain within the scope of the invention defined by the appended claims.

What is claimed is:

1. A method of thermally insulating a surface, the method comprising applying a coating of a thermally insulating composition onto said surface, wherein said thermally insulating composition comprises:
   (i) hollow spherical nanoparticles having a mean particle size of less than 800 nm in diameter and a particle size distribution in which at least 90% of the hollow spherical nanoparticles have a size within ±20% of said mean particle size, and a first layer of cationic or anionic molecules attached to surfaces of the hollow spherical nanoparticles; and
   (ii) a second layer of molecules of opposite charge to the first layer of molecules, wherein said second layer of molecules of opposite charge are ionically associated with said first layer of molecules, wherein the molecules in said second layer have at least eight carbon atoms.

2. The method of claim 1, wherein said hollow spherical nanoparticles have an inorganic composition.

3. The method of claim 2, wherein said inorganic composition is a metal oxide composition.

4. The method of claim 3, wherein said metal oxide composition is a silicon oxide composition.

5. The method of claim 1, wherein said hollow spherical nanoparticles have an organic composition.

6. The method of claim 1, wherein said hollow spherical nanoparticles have a mean particle size of no more than 500 nm.

7. The method of claim 1, wherein said hollow spherical nanoparticles have a mean particle size of no more than 200 nm.

8. The method of claim 1, wherein said hollow spherical nanoparticles have a mean particle size of no more than 100 nm.

9. The method of claim 1, wherein said surfaces of the hollow spherical nanoparticles contain pores having a size of up to or less than 50 nm.

10. The method of claim 9, wherein said pores have a size of up to or less than 20 nm.

11. The method of claim 9, wherein said pores have a size of up to or less than 10 nm.

12. The method of claim 9, wherein said pores have a size of up to or less than 5 nm.

13. The method of claim 1, wherein said thermally insulating composition is a liquid at 25° C.

14. The method of claim 13, wherein said thermally insulating composition behaves as a room temperature ionic liquid.

15. The method of claim 1, wherein said thermally insulating composition is transparent.

16. The method of claim 1, wherein said thermally insulating composition is coated onto glass.

17. The method of claim 16, wherein said glass is part of a window.

18. The method of claim 1, wherein said thermally insulating composition is coated onto a structural material.

19. The method of claim 1, wherein said thermally insulating composition is coated onto a paper or plastic product useful in holding a food or beverage.

20. The method of claim 1, wherein said thermally insulating composition is coated onto a fabric.

21. The method of claim 1, wherein said thermally insulating composition is coated onto skin.

22. The method of claim 1, wherein said thermally insulating composition is coated onto a metal.

23. The method of claim 22, wherein said metal is shaped as a pipe.

24. The method of claim 1, wherein said cationic molecules are silane molecules.

* * * * *